United States Patent
Kilpela et al.

[11] Patent Number: 5,935,130
[45] Date of Patent: *Aug. 10, 1999

[54] CABLE TENSIONING DEVICE

[75] Inventors: Thomas S. Kilpela, Marquette; Francis J. Korhonen, Negaunee, both of Mich.; Rober J. Songer, Northbrook, Ill.; Matthew N. Songer, Marquette, Mich.

[73] Assignee: Pioneer Laboratories, Inc., Marquette, Mich.

[*] Notice: This patent is subject to a terminal disclaimer.

[21] Appl. No.: 08/923,043

[22] Filed: Sep. 3, 1997

Related U.S. Application Data

[62] Division of application No. 08/616,687, Mar. 15, 1996, Pat. No. 5,788,697, which is a continuation of application No. 08/201,102, Feb. 24, 1994, abandoned.

[51] Int. Cl.⁶ .................................................. A61B 17/56
[52] U.S. Cl. ............................................. 606/74; 606/103
[58] Field of Search .................................. 606/74, 72, 60, 606/103, 86; 254/199, 230, 231, 232

[56] References Cited

U.S. PATENT DOCUMENTS

| | | |
|---|---|---|
| 2,049,361 | 7/1936 | Ericsson . |
| 3,111,945 | 11/1963 | Solbrig . |
| 3,438,406 | 4/1969 | Rozmus . |
| 3,507,270 | 4/1970 | Ferrier . |
| 5,057,113 | 10/1991 | Mingozzi . |
| 5,071,420 | 12/1991 | Paulos et al. . |
| 5,116,340 | 5/1992 | Songer et al. . |
| 5,236,434 | 8/1993 | Callicrate . |
| 5,312,410 | 5/1994 | Miller et al. . |
| 5,395,374 | 3/1995 | Miller et al. . |
| 5,415,658 | 5/1995 | Kilpela et al. . |
| 5,536,270 | 7/1996 | Songer et al. . |

*Primary Examiner*—Guy V. Tucker
*Attorney, Agent, or Firm*—Gerstman, Ellis & McMillin, Ltd.

[57] ABSTRACT

A cable tensioning device comprises tubular shaft having an outer threaded portion, and a handle member surrounding a portion of the shaft, with the shaft and handle member being connected in screw-threaded relation. The shaft moves longitudinally relative to the handle as the handle rotates, driven by the screw threaded connection. A gripping member is carried on the shaft distal to the handle member for holding a replaceable bit, which, in turn, may carry a cable crimp. A cable lock is positioned typically proximal of the handle member to hold the ends of cables extending through the tubular shaft. Rotation of the handle member can cause the shaft to move longitudinally to lengthen the distance between the cable lock and a crimp held by a bit which, in turn, is held by the gripping member, to impose a tension on the cable. A meter is present for measuring the amount of tension applied to the cable.

18 Claims, 4 Drawing Sheets

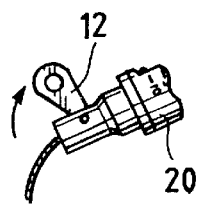
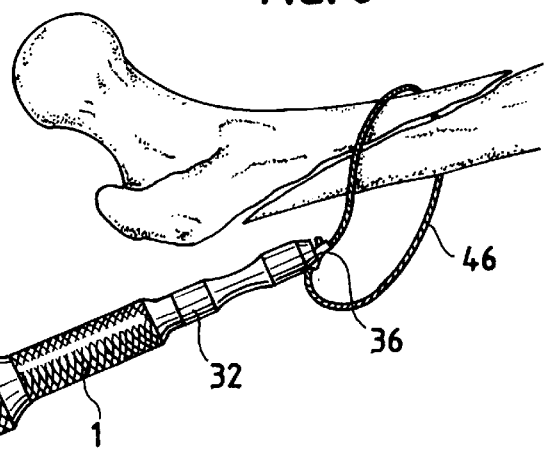
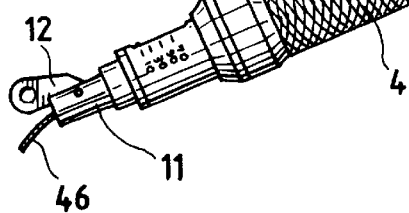
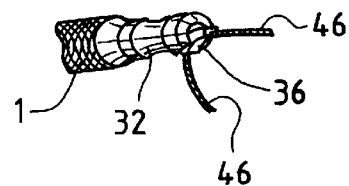
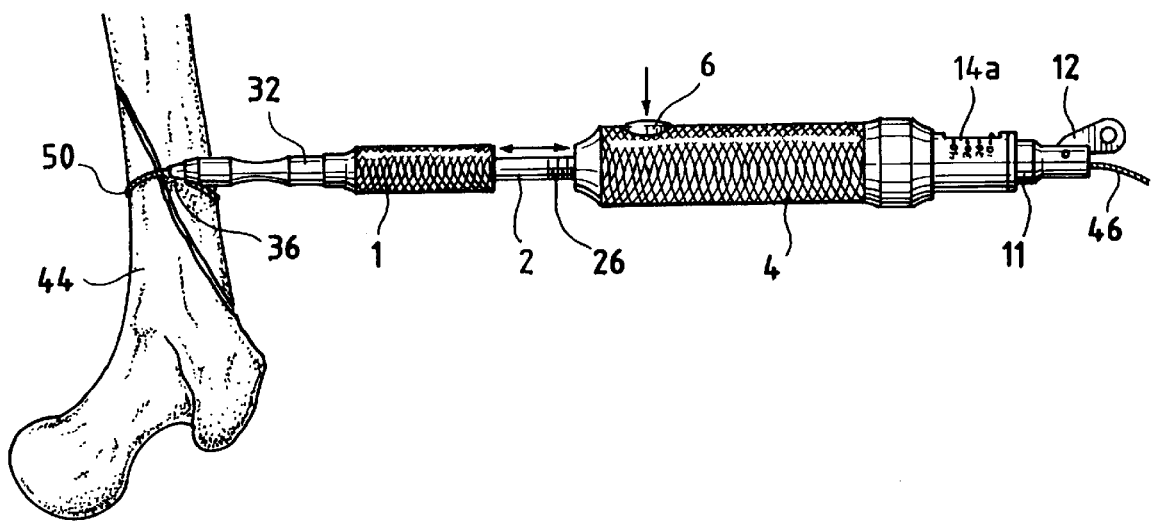

CABLE TENSIONING DEVICE

CROSS REFERENCE TO RELATED APPLICATION

This application is a division of application Ser. No. 08/616,687, filed Mar. 15, 1996, now U.S. Pat. No. 5,788,697, which, in turn is a continuation of application Ser. No. 08/201,102, filed Feb. 24, 1994 now abandoned.

BACKGROUND OF THE INVENTION

Orthopedic cables are used to strengthen and repair broken bones. The cables are typically formed into a loop, simple or complex, and tightened about the bone structure with a tensioning tool. See for example Songer et al. U.S. Pat. No. 5,116,340.

There remains a need for a cable tensioner which has a narrow, thin design so that it can penetrate into small, deep wounds and incisions for tensioning of cables deeply mounted in the body.

Also, it would be desirable to provide a cable tensioning unit having the flexibility to engage a wide variety of different cable crimps, as well as being usable in other cable tensioning operations. For example, the cable tensioner might press against a bone plate rather than holding a crimp in the cable tensioning process.

By this invention, such a narrow, thin, but versatile cable tensioner is provided which is capable of gripping a wide variety of cable crimps, or merely providing pressure against bone plates or the like as part of the tensioning process.

The cable tensioner apparatus is also capable of providing a specific, predetermined level of tension which may be variable on a moment-to-moment basis as the surgeon may decide. Also, the process of the tensioning is convenient in its operation and quick.

DESCRIPTION OF THE INVENTION

By this invention a cable tensioning device is provided which comprises: a tubular shaft having an outer threaded portion and a handle member surrounding a portion of the shaft. The handle member carries the shaft in a manner permitting a relative rotation which causes the shaft to move longitudinally relative to the handle as the handle rotates. This is preferably accomplished by connecting the tubular shaft and handle member together in screw-threaded relation.

A gripping member is carried on the shaft distal to the handle member for holding a cable crimp, typically by use of a replaceable bit which, in turn, can releasably carry a cable crimp or be otherwise used in a crimping function, for example by pressing against a bone plate to provide purchase for tensioning. The bit is replaceable, typically in a conventional manner of tool bits, so that different bits may be used for receiving different cable crimps or for performing other desired tensioning functions.

A cable lock is positioned on a portion of the tensioning device which is typically proximal to the handle member, and does not rotate with the handle member, to hold the ends of cables extending through the tubular shaft. Any suitable conventional cable lock mechanism may be used.

Accordingly, rotation of the handle member can cause the shaft to move longitudinally without rotation, to lengthen the distance between the cable lock and the bit which is held by the gripping member, to impose a tension on the cable.

Also, a meter, carried by the tensioning device, is provided for measuring the tension, so that the surgeon can apply a specific, quantitative tension as desired to a cable by means of the tensioning device of this invention.

The handle member preferably defines a bore having an internally threaded section of no more than about 180 degrees extent around the bore, and typically less. The tubular shaft extends through the bore and defines external threads that normally engage the internally threaded section. Means, such as a spring-biased push button, are provided for temporarily moving the internally threaded section out of engagement with the external threads, to permit the shaft to freely slide in the bore of the handle member. Thus, when tensioning is desired, the threads may be disengaged and the shaft may be manually extended from the handle member to a position where the tensioning begins. Then, the threads may be reengaged, and the handle rotated to provide a quantitatively determinable tension (through the meter) on the cable as desired. Thus, a substantial saving in time is provided by this means for temporarily moving the internally threaded section out of engagement with the external threads, so that the shaft may be quickly advanced to the position where tensioning of the cable begins.

The meter typically comprises a longitudinally sliding portion of the device, relative to the handle member, typically positioned at the proximal end of the meter. A spring is positioned to resist sliding of this portion toward the gripping member. An indicator or meter is provided of the amount of such sliding as the cable is tensioned, responsive to the degree of deflection of the spring. Because the cable lock is carried on this sliding portion, increased tension of the cable results in more deflection of the spring. The indicator may be an arrow which slides along a scale, indicating the quantitative amount of tension as the spring is depressed by that tension.

DESCRIPTION OF THE DRAWINGS

In the drawings,

FIGS. 5–11 show sequential steps for performing cerclage of a cable around a broken bone to secure the bone together, using the cable tensioning device of this invention.

DESCRIPTION OF SPECIFIC EMBODIMENTS

Figure 1:
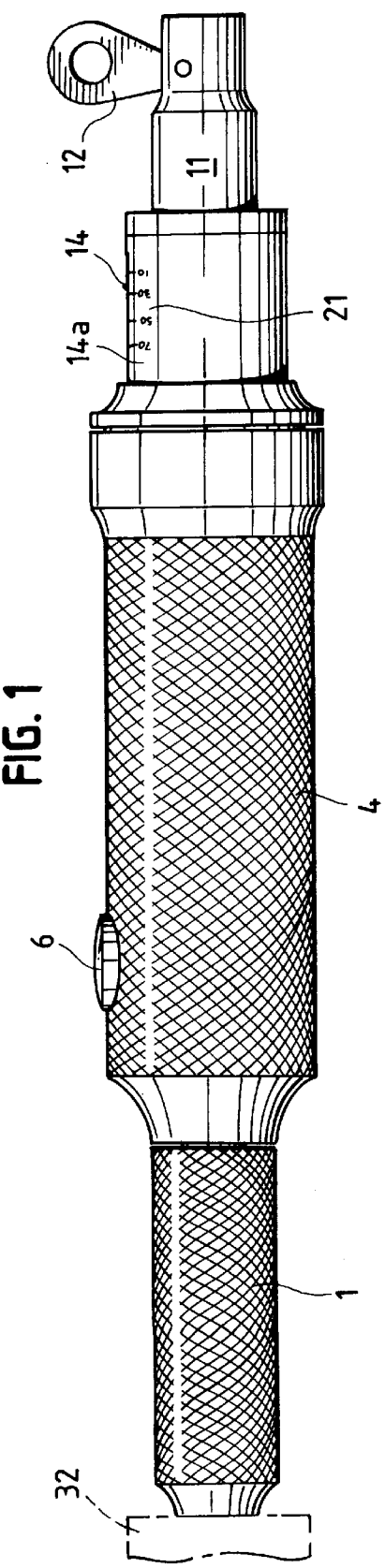
FIG. 1 is an elevational view of the cable tensioning device of this invention.

Referring to FIGS. 1–4, the cable tensioning device of this invention comprises a main tubular shaft 2 (FIG. 2) having a distal end upon which is carried gripping member or fore grip 1. Shaft 2 defines a hexagonal socket 2a and a split ring retention spring 3 for receiving a tubular extension 30 of a bit 32 therein (FIG. 3), with spring 3 fitting into annular groove 34 of the extension 30 in conventional manner.

Handle member 4 surrounds shaft 2, part of which resides in bore 4a of the handle member. Handle member 4 terminates at handle cap 5 at its proximal end. Handle member 4 also defines a proximal aperture in which is placed a spring housing 8, retained by spring housing pin 9, which presses against a flat portion of tubular shaft 2 so that shaft 2 does not rotate with handle 4. Spring 17 is shown, being retained by spring housing 8 at one end and cam body 11 on the other end. Cam body 11, in turn, is retained in position by spring housing cap 10.

A rotatable cam lock 12 is carried on cam body 11 by a cam pin 13. Nose 13a of cam body 12 is capable of rotating into recess 11a and rotating back into the position shown in FIG. 2 where nose 13a is spaced from recess 11a. For tensioning, cable passing through a cable crimp 36 may pass through bore 38 of bit 32, which is carried on the end of gripping member 1. The cable also extends through the bore 2c of shaft 2 along essentially the entire length of the cable tensioning device until it enters into engagement with cam lock 12, which retains the cable by rotating into its horizontal position where nose 13a enters into space 11a, with the cable also occupying the space 11a.

Figure 2:
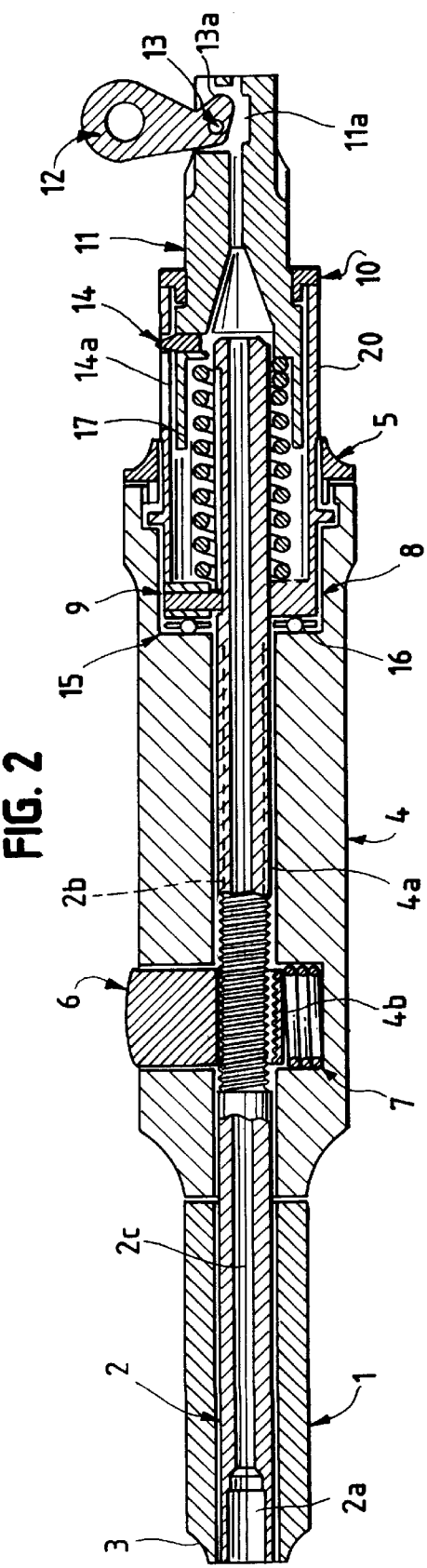
FIG. 2 is a longitudinal sectional view of the device of FIG. 1.

After this has been accomplished, the user may press button 6, which is biased by spring 7 into its position as shown in FIG. 2, to downwardly displace a threaded portion 4b which normally engages the threads of threaded portion 2b of shaft 2. The threads 2b of shaft 2 extend along a central portion thereof completely around the shaft, while the threaded portion 4b serves as the internally threaded section of the bore 4a of handle member 4, having an extent of no more than about 180 degrees around the bore, and typically less than that. Thus, when button 6 is depressed, causing disengagement of the threads 2b and 4b, one can manually advance gripping member 1 until the cable extending through the tensioning device loses all of its slack and tensioning begins. Then, upon release of button 6, the respective threads 2b, 4b reengage.

Following this, handle 4 can be rotated whereby the non-rotating shaft 2 is impelled to move longitudinally relative to the handle, to further lengthen the tensioning device and to impose tension upon the cable. As this takes place, cam body 11 and cam lock 12 are placed under a force that is equal to and opposite of the tension on the cable, urging cam body 11 to the left as shown in FIG. 2. As this takes place, scale blade 14 moves with cam body 11 to the left, against the spring, with scale blade 14 moving along slot 14a along the scale of indicia 21 associated with slot 14a, as shown in FIG. 1. This motion is of course responsive to the force imposed on spring 17, so that an accurate measurement of the cable tension can be achieved simply by noting the position of scale blade 14 at any given time.

Then, when the desired tension has been achieved, in the specific process shown, the crimp 36 may be tightened to retain the cable in a permanently tensioned configuration. The specific design of crimp 36 shown in FIG. 3 may be the specific crimp disclosed in Kilpela et al. U.S. patent application Ser. No. 08/167,542, filed Dec. 14, 1993, now U.S. Pat. No. 5,415,658. However, many different and conventional designs of crimps may be used with the cable tensioning device of this invention.

Crimp 36 is shown to slidingly fit into a slot 40 of bit 32, which, in turn, is carried by the cable tensioning device. Bit 32 also may define a central portion 42 which is radiused inwardly as shown, to facilitate the user in gripping the bit to easily engage and disengage it with the tensioner device.

A nylon spacer 15 and ball bearings 16 facilitate the rotation of handle 4, while the rear spring 17 and its housing 20 are non-rotating, and retain shaft 2 and gripping member 1 in non-rotating relation as well.

Figure 3:
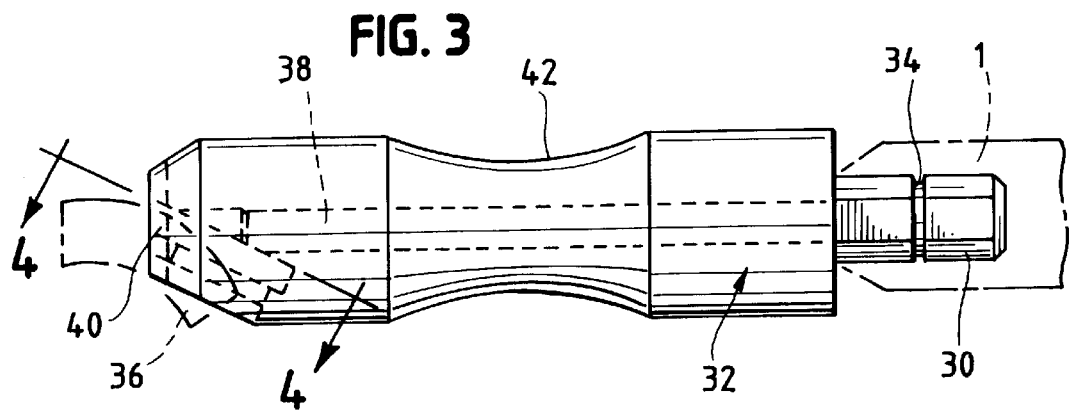
FIG. 3 is an elevational view of a bit for holding a cable crimp, and for attachment to the gripping member of the cable tensioning device of FIGS. 1 and 2.
Figure 4:
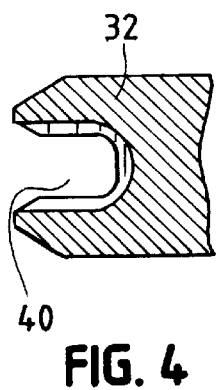
FIG. 4 is a sectional view taken along line A—A of FIG. 3.

In FIGS. 1, 3 and 4, typical preferred dimensions of the cable tensioning device are shown, being expressed in inches.

Referring to FIGS. 5 through 11, various sequential steps are shown of a cable-ready cerclage technique for a broken bone, making use of the cable tensioning device of this invention.

Figure 5A:
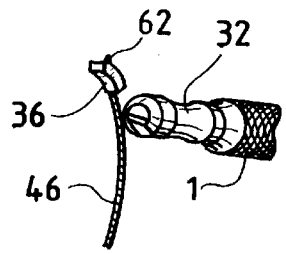
Figure 5B:
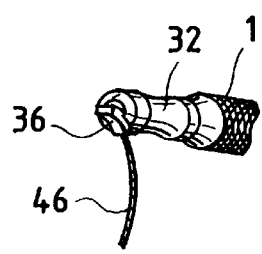
Figure 5:
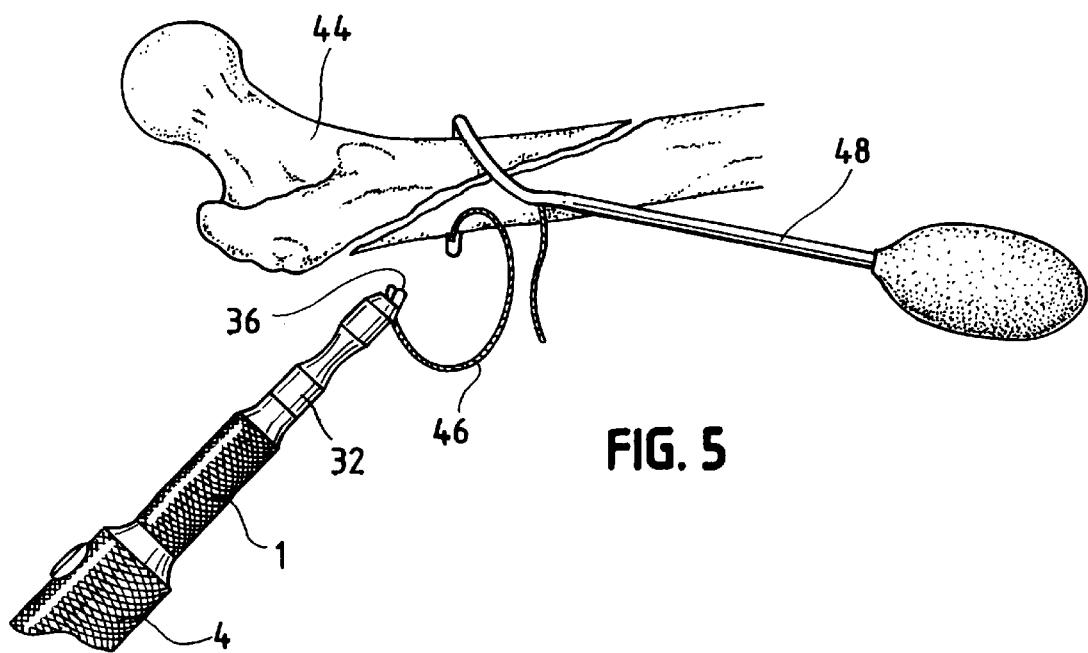

FIG. 5 is a partially schematic view of a surgical procedure showing a broken bone 44 (without the other tissues of the patient) and showing an initial step for applying a cable about the bone to secure it together. The cerclage cable 46 is inserted into a crimp 36 of a specific design described in the previously cited patent application, which crimp is carried by attachment bit 32. Bit 32 is, in turn, carried in gripping member 1 of the tensioning device of this invention, as previously described.

FIGS. 5a and 5b show front perspective views of how cerclage cable 46 is attached to crimp 36, and crimp 36 slides into the front end of bit 32 in a manner similar to that indicated in FIG. 3.

Cable 46 is looped around bone 44 with the assistance of a conventional cable passer 48 if desired.

Then, as shown in FIG. 6, the free end of cerclage cable 46 forms a loop, being passed a second time through the crimp 36 as shown. One pulls slack to tighten the loop of cable 46, and then locks the cable by moving cam lock lever 12 from the open position of FIG. 7 to the closed position of FIG. 6, where the cable 46, which extends through the entire length of the tensioning device, is locked by the action of cam lock 12 as previously described. The double threaded aspect of cable 46 through crimp 36 is illustrated in FIG. 8.

Referring to FIG. 9, one then depresses button 6, which disengages the respective screw threads 4b from the threads 2b on shaft 2, permitting advancement of gripping member 1 and shaft 2 with free sliding to place an initial tension on the cable loop 50 about bone 44. One then releases button 6 to cause the threads of shaft 2 to once again engage threads 4b carried by handle 4.

Figure 10:
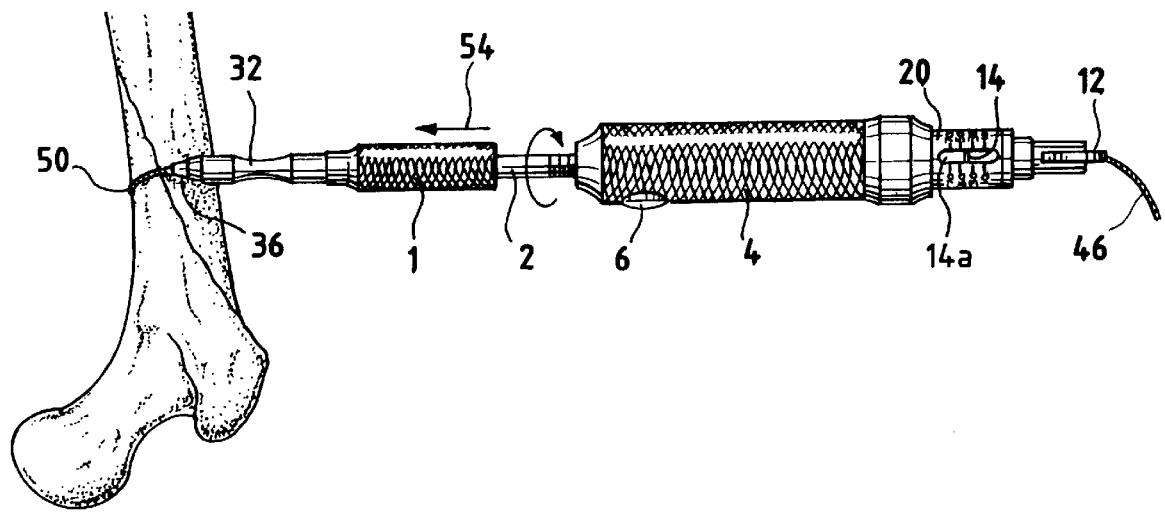

Then, as shown in FIG. 10, one rotates handle 4 relative to proximal housing 20, shaft 2, and gripping member 1, as well as bit 32 and crimp 36. Upon such rotation, shaft 2 and the other parts extend in the direction of arrow 54, being driven by the interengagement of the respective threads 2b, 4b, causing a lengthening of the tensioning device while cable 46 is firmly held by cam lock 12. As previously described, spring 17 is depressed as cam body 11 is pulled by cable 46 against spring 17 and as the remainder of the tensioning device lengthens. Accordingly, scale blade 14 advances along slot 14a which is bracketed by the numerical indicia 21 as shown, indicating the level of tension being applied to cable 46 and its loop 50. Rotation of handle 4 is terminated when scale blade 14 indicates the achievement of the desired, numerical degree of tension. By this apparatus, the same tension can be applied time after time on an accurate, quantitative basis to various cerclage cables looped around bones, or for any other desired purpose.

Figure 11:
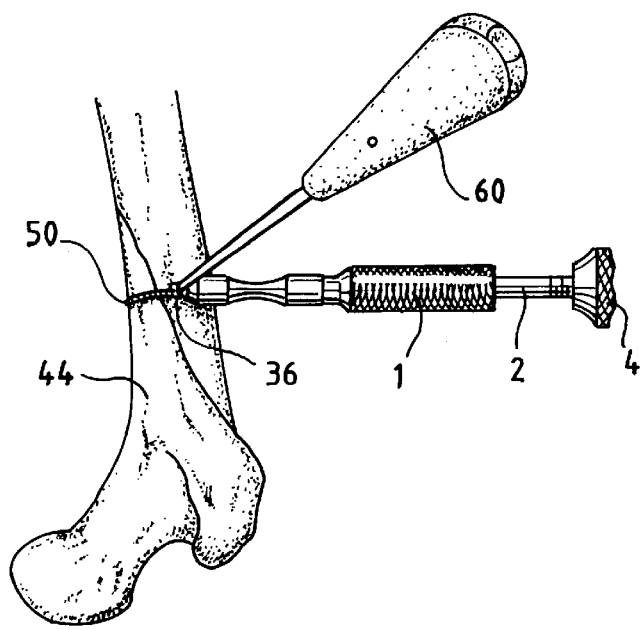

Then, in FIG. 11, a hex screw driver 60 rotates the screw 62 (FIG. 5a) carried on crimp 36 to lock the cable loop 50 into permanent attachment at the predetermined tension around the bone 44. Alternatively, crimping pliers may be applied to collapse the crimp, if crimps which are collapsed in that manner are used. Then, the cable tensioning device of this invention is disengaged from crimp 36 by allowing the crimp to slide out of slot 40, and the cerclage is complete.

Bit 32 is non-rotatable because its stem 30 may be of hexagonal or other non-circular cross section, fitting into a recess 2a at the distal end of shaft 2 of similar hexagonal or other non-circular cross section.

Thus, a cable tensioning device is provided having significant advantages, in that the tensioner has a narrow design allowing it to penetrate deeply into the patient with a smaller incision. Also, the device of this invention is adapted for use with multiple attachment bits, permitting its use with a wide variety of desired crimps or for other tensioning purposes as well. While the tensioner can be lengthened for tensioning a cable by rotating of handle 4, a push button thread release is also provided, for quick, initial tensioning to provide significant time savings.

The tensioner of this invention is capable of accurately reproducing a desired cable tension time after time, which cable tension may be quantitatively expressed in terms of the units used in the meter for measuring tension.

The above has been offered for illustrative purposes only, and is not intended to limit the scope of this invention, which is as defined in the claims below.

That which is claimed:

1. A cable tensioning device which comprises:
   a tubular shaft having an outer threaded portion;
   a handle member having an inner, threaded bore surrounding a portion of said shaft, said handle member carrying internal threads to engage said shaft in a threadedly engaged manner permitting rotation and causing said shaft to move longitudinally relative to said handle member as the handle member rotates;
   a retaining member carried on said shaft distal to said handle member holding a cable crimp; a cable carried by said cable crimp and extending through and within said tubular shaft; and
   a cable lock positioned to hold said cable extending through said tubular shaft, whereby rotation of said handle member can cause said shaft to move longitudinally to lengthen the distance between said cable lock and said crimp held by said retaining member, to impose a tension on said cable.

2. The cable tensioning device of claim 1 in which said retaining member carries an interchangeable bit for holding a specific design of cable crimp, whereby various bits of differing design can be sequentially used with said device to hold different designs of crimps.

3. The cable tensioning device of claim 1 in which said handle member defines a bore with an internally threaded section of no more than about 180 degrees extent around said bore, said tubular shaft defining external threads that normally engage said internally threaded section, and a member for temporarily moving said internally threaded section out of engagement with the external threads to permit the shaft to freely slide in the bore of said handle member.

4. The cable tensioning device of claim 1 which comprises a meter having a longitudinally sliding portion relative to said handle member, a spring positioned to resist sliding of said portion toward said gripping member, and an indicator of the amount of said sliding as cable within said shaft is tensioned, said cable lock being carried on said sliding portion.

5. The cable tensioning device of claim 1 in which said shaft is unitary and integral along its entire length.

6. A cable tensioning device which comprises:
   a tubular shaft having an outer threaded portion;
   a handle member surrounding a portion of said shaft, said handle member defining a bore with an internally threaded section of no more than about 180 degrees extent around said bore, said tubular shaft defining external threads that normally engage said internally threaded section, and apparatus for temporarily moving said internally threaded section out of engagement with the external threads to permit the shaft to freely slide in the bore of said handle member, said shaft being movable relative to said handle as the handle rotates with threads engaged;
   a retaining member carried on said shaft distal to said handle member for holding a replaceable bit which holds a cable crimp;
   a cable lock to hold the ends of cables extending through said tubular shaft, whereby rotation of said handle member can cause said shaft to move longitudinally to lengthen the distance between said cable lock and said crimp held by said retaining member, to impose a tension on said cable; and
   a meter for measuring said tension carried by said device.

7. The cable tensioning device of claim 6 in which said meter comprises a longitudinally sliding portion relative to said handle member, a spring positioned to resist sliding of said portion toward said gripping member, and an indicator of the amount of said sliding as cable is tensioned, said cable lock being carried on said sliding portion.

8. The cable tensioning device of claim 7 in which said cable lock is positioned proximal of said handle member.

9. The cable tensioning device of claim 6 in which said tubular shaft is unitary and integral along its entire length, and carrying said handle member.

10. A cable tensioning system which comprises:
    a tubular shaft having an outer threaded portion;
    a handle member having an inner, threaded bore surrounding a portion of said shaft, said handle member carrying internal threads to engage said shaft in a threadedly engaged manner permitting rotation and causing said shaft to move longitudinally relative to said handle member as the handle member rotates;
    a retaining member associated with said shaft and positioned distal to said handle member, said retaining member holding a cable crimp and a cable carried by said crimp for crimping attachment thereto, said cable also extending through said tubular shaft;
    a cable lock positioned to hold said cable extending through said tubular shaft, whereby rotation of said handle member can cause said shaft to move longitudinally along said screw threads to lengthen the distance between said cable lock and said crimp held by said retaining member, to impose a tension on said cable; and
    an indicator of the amount of tension on the cable, said indicator and cable lock being carried on a spring-biased, longitudinally movable portion of said handle member.

11. The cable tensioning device of claim 10 in which said handle member defines a bore with an internally threaded section of no more than about 180 extent around said bore, said tubular shaft defining external threads that normally engage said internally threaded section, and a member for temporarily moving said internally threaded section out of engagement with the external threads, to permit the shaft to freely slide in the bore of said handle member.

12. The cable tensioning device of claim 11 in which said retaining member carries an interchangeable bit for holding a specific design of cable crimp, whereby various bits of differing design can be sequentially used with said device to hold different designs of crimps.

13. A cable tensioning device which comprises:
    a tubular shaft having an outer, threaded portion;
    a manually rotatable member having an inner, threaded bore surrounding a portion of said shaft, said manually rotatable member carrying internal threads to engage said shaft in a threadedly engaged manner permitting rotation and causing such shaft to move longitudinally relative to said manually rotatable member as the manually rotatable member rotates;

a retaining member carried on said device distal to said manually rotatable member;

a cable crimp engaging said retaining member;

a cable carried by said cable crimp and extending through and within said tubular shaft; and a cable lock positioned to hold said cable extending through said tubular shaft, whereby rotation of said manually rotatable member can cause said shaft to move longitudinally to lengthen the distance between said cable lock and said cable crimp engaging said retaining member, to impose a tension on said cable.

14. The cable tensioning device of claim 13 which comprises a meter having a longitudinally sliding portion relative to said manually rotatable member, a spring positioned to resist sliding of said sliding portion, and an indicator of the amount of said sliding as cable within said shaft is tensioned.

15. The cable tensioning device of claim 13 in which said manually rotatable member defines a bore with an internally threaded section of no more than about 180 degrees extent around said bore, said tubular shaft defining external threads that normally engage said internally threaded section, and a member for temporarily moving said internally threaded section out of engagement with the external threads to permit the shaft to freely slide in the bore of said manually rotatable member.

16. The cable tensioning device of claim 13 in which said cable lock is positioned proximally of said manually rotatable member.

17. The cable tensioning device of claim 13 in which said shaft is unitary and integral along its entire length.

18. The cable tensioning device of claim 13 in which said cable lock does not rotate with the manually rotatable member.

* * * * *